United States Patent
Virshup et al.

(10) Patent No.: US 9,530,196 B2
(45) Date of Patent: Dec. 27, 2016

(54) REDUCING HEEL EFFECT IN DUAL ENERGY X-RAY IMAGES

(71) Applicant: VARIAN MEDICAL SYSTEMS, INC., Palo Alto, CA (US)

(72) Inventors: Gary F. Virshup, Cupertino, CA (US); Arundhuti Ganguly, San Jose, CA (US)

(73) Assignee: VARIAN MEDICAL SYSTEMS, INC., Palo Alto, CA (US)

(*) Notice: Subject to any disclaimer, the term of this patent is extended or adjusted under 35 U.S.C. 154(b) by 35 days.

(21) Appl. No.: 14/696,937

(22) Filed: Apr. 27, 2015

(65) Prior Publication Data

US 2016/0314568 A1    Oct. 27, 2016

(51) Int. Cl.
| | | |
|---|---|---|
| G06K 9/00 | (2006.01) |
| G06T 5/50 | (2006.01) |
| A61B 6/00 | (2006.01) |
| G01N 23/087 | (2006.01) |
| G06T 5/00 | (2006.01) |

(52) U.S. Cl.
CPC .......... *G06T 5/50* (2013.01); *A61B 6/482* (2013.01); *G01N 23/087* (2013.01); *G06T 5/009* (2013.01); *G06T 2207/10116* (2013.01); *G06T 2207/20021* (2013.01); *G06T 2207/20208* (2013.01); *G06T 2207/20221* (2013.01)

(58) Field of Classification Search
None
See application file for complete search history.

(56) References Cited

U.S. PATENT DOCUMENTS

| | | | |
|---|---|---|---|
| 6,408,050 B1* | 6/2002 | Han | G01T 1/17 378/98.11 |
| 8,422,757 B2* | 4/2013 | Fei | A61B 6/12 382/132 |
| 9,271,688 B2* | 3/2016 | Das | A61B 6/481 |
| 2003/0053671 A1 | 3/2003 | Dewaele et al. | |
| 2008/0192898 A1* | 8/2008 | VanMetter | G06T 11/008 378/98.9 |
| 2009/0129659 A1* | 5/2009 | Deutschmann | A61N 5/1048 382/132 |
| 2009/0310886 A1 | 12/2009 | Kitamura | |
| 2010/0264918 A1* | 10/2010 | Roeck | G01R 33/481 324/307 |
| 2011/0216959 A1 | 9/2011 | Kuwabara | |
| 2013/0108021 A1* | 5/2013 | Durst | G01N 23/207 378/71 |

OTHER PUBLICATIONS

International Search Report and Written Opinion dated Sep. 7, 2016 as received in Application No. PCT/US2016/029386 (10 pgs.).

* cited by examiner

*Primary Examiner* — Shervin Nakhjavan
(74) *Attorney, Agent, or Firm* — Maschoff Brennan (57) ABSTRACT

In some examples, a method to reduce heel effect distortion in dual energy x-ray images includes receiving flood field images generated by x-rays at different energy levels and generating one or more normalize images based on the flood field images. The method may also include applying the one or more normalize images to one or more x-ray images and combining the x-ray images to generate a dual energy x-ray image with reduced heel effect distortion.

20 Claims, 7 Drawing Sheets

REDUCING HEEL EFFECT IN DUAL ENERGY X-RAY IMAGES

FIELD

Embodiments disclosed herein relate generally to dual energy x-ray images. More particularly, example embodiments relate to reducing distortion caused by heel effect in dual energy x-ray images.

BACKGROUND

Unless otherwise indicated herein, the materials described in this section are not prior art to the claims in the present application and are not admitted to be prior art by inclusion in this section.

X-ray tubes are used in a variety of industrial and medical applications. For example, x-ray tubes are employed in medical diagnostic examination, therapeutic radiology, semiconductor fabrication, and material analysis. Regardless of the application, most x-ray tubes operate in a similar fashion. X-rays, which are high frequency electromagnetic radiation, are produced in x-ray tubes by applying an electrical current to a cathode to cause electrons to be emitted from the cathode by thermionic emission. The electrons accelerate towards and then impinge upon an anode. The distance between the cathode and the anode is generally known as A-C spacing or throw distance. When the electrons impinge upon the anode, the electrons can collide with the anode to produce x-rays. The area on the anode in which the electrons collide is generally known as a focal spot.

X-rays can be produced through at least two mechanisms that can occur during the collision of the electrons with the anode. A first x-ray producing mechanism is referred to as x-ray fluorescence or characteristic x-ray generation. X-ray fluorescence occurs when an electron colliding with material of the anode has sufficient energy to knock an orbital electron of the anode out of an inner electron shell. Other electrons of the anode in outer electron shells fill the vacancy left in the inner electron shell. As a result of the electron of the anode moving from the outer electron shell to the inner electron shell, x-rays of a particular frequency are produced. A second x-ray producing mechanism is referred to as Bremsstrahlung. In Bremsstrahlung, electrons emitted from the cathode decelerate when deflected by nuclei of the anode. The decelerating electrons lose kinetic energy and thereby produce x-rays. The x-rays produced in Bremsstrahlung have a spectrum of frequencies. The x-rays produced through either Bremsstrahlung or x-ray fluorescence may then exit the x-ray tube to be utilized in one or more of the above-mentioned applications.

The subject matter claimed herein is not limited to embodiments that solve any disadvantages or that operate only in environments such as those described above. Rather, this Background Section is provided to illustrate one exemplary technology area where embodiments of the present disclosure described herein may be practiced.

SUMMARY

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter. The object and advantages of the implementations will be realized and achieved at least by the elements, features, and combinations particularly pointed out in the claims.

Technologies described herein generally relate to dual energy x-ray images.

In one embodiment, a method to reduce heel effect distortion in dual energy x-ray images may include receiving a first flood field image generated by x-rays at a first energy level, a second flood field image generated by x-rays at a second energy level, a first x-ray image generated by x-rays at the first energy level and a second x-ray image generated by x-rays at the second energy level. The method may also include generating a normalize image based on the first flood field image and the second flood field image, and applying the normalize image to the second x-ray image to generate a normalized second x-ray image. The method may further include combining the first x-ray image with the normalized second x-ray image to generate a dual energy x-ray image.

In one embodiment, a system to reduce heel effect distortion in dual energy x-ray images may include a normalize module configured to receive a first flood field image generated by x-rays at a first energy level and a second flood field image generated by x-rays at a second energy level. The normalize module may generate a normalize image based on the first flood field image and the second flood field image. The system may also include a dual energy module configured to receive a first x-ray image generated by x-rays at the first energy level and a second x-ray image generated by x-rays at the second energy level. The dual energy module may apply the normalize image to the second x-ray image to generate a normalized second x-ray image and combine the first x-ray image with the normalized second x-ray image to generate a dual energy x-ray image.

In one embodiment, a method to reduce heel effect distortion in dual energy x-ray images may include receiving a first flood field image generated by x-rays at a first energy level, a second flood field image generated by x-rays at a second energy level, a third flood field image generated by x-rays at a third energy level, a first x-ray image generated by x-rays at the first energy level, and a second x-ray image generated by x-rays at the second energy level. The method may also include generating first and second normalize images based on the first, second, and third flood field images and applying the first and second normalize images to the first and second x-ray images to generate first and second normalized x-ray images. The method may further include combining the normalized first and second x-ray images to generate a dual energy x-ray image.

The foregoing summary and the following detailed description are exemplary, explanatory, and illustrative only and are not restrictive of the invention, as claimed. In addition to the illustrative aspects, embodiments, advantages, and features described above, additional aspects, embodiments, advantages, and features will be set forth in the following description and claims, and in part will be obvious from the description and claims, or may be learned by the practice of the teachings herein.

BRIEF DESCRIPTION OF THE DRAWINGS

The foregoing and following information, as well as other features of this disclosure, will become more fully apparent from the following description and appended claims, taken in conjunction with the accompanying drawings. Understanding that these drawings depict only typical embodiments in accordance with this disclosure, and are therefore not to be considered limiting of its scope, the disclosure will be described and explained with additional specificity and detail through use of the accompanying drawings in which:

DETAILED DESCRIPTION OF IMPLEMENTATIONS

In the following detailed description, reference is made to the accompanying drawings that show, by way of illustration, exemplary embodiments of the invention. In the drawings, similar symbols typically identify similar components, unless context dictates otherwise. These embodiments are described in sufficient detail to enable those skilled in the art to practice the invention. Other embodiments may be utilized and structural, logical, and electrical changes may be made without departing from the spirit or scope of the subject matter presented herein. Moreover, it is to be understood that the various embodiments of the invention, although different, are not necessarily mutually exclusive. For example, a particular feature, structure, or characteristic described in one embodiment, in the figures, or generally described herein, may be included, arranged, substituted, combined, separated, and designed within other embodiments in a wide variety of different configurations, all of which are explicitly contemplated herein. Accordingly, it will be readily understood that the present invention, as generally described and illustrated in the figures herein, could vary in a wide range. The following detailed description is, therefore, not to be taken in a limiting sense, and the scope of the present invention is defined only by the appended claims, along with the full scope of equivalents to which such claims are entitled.

Figure 1:
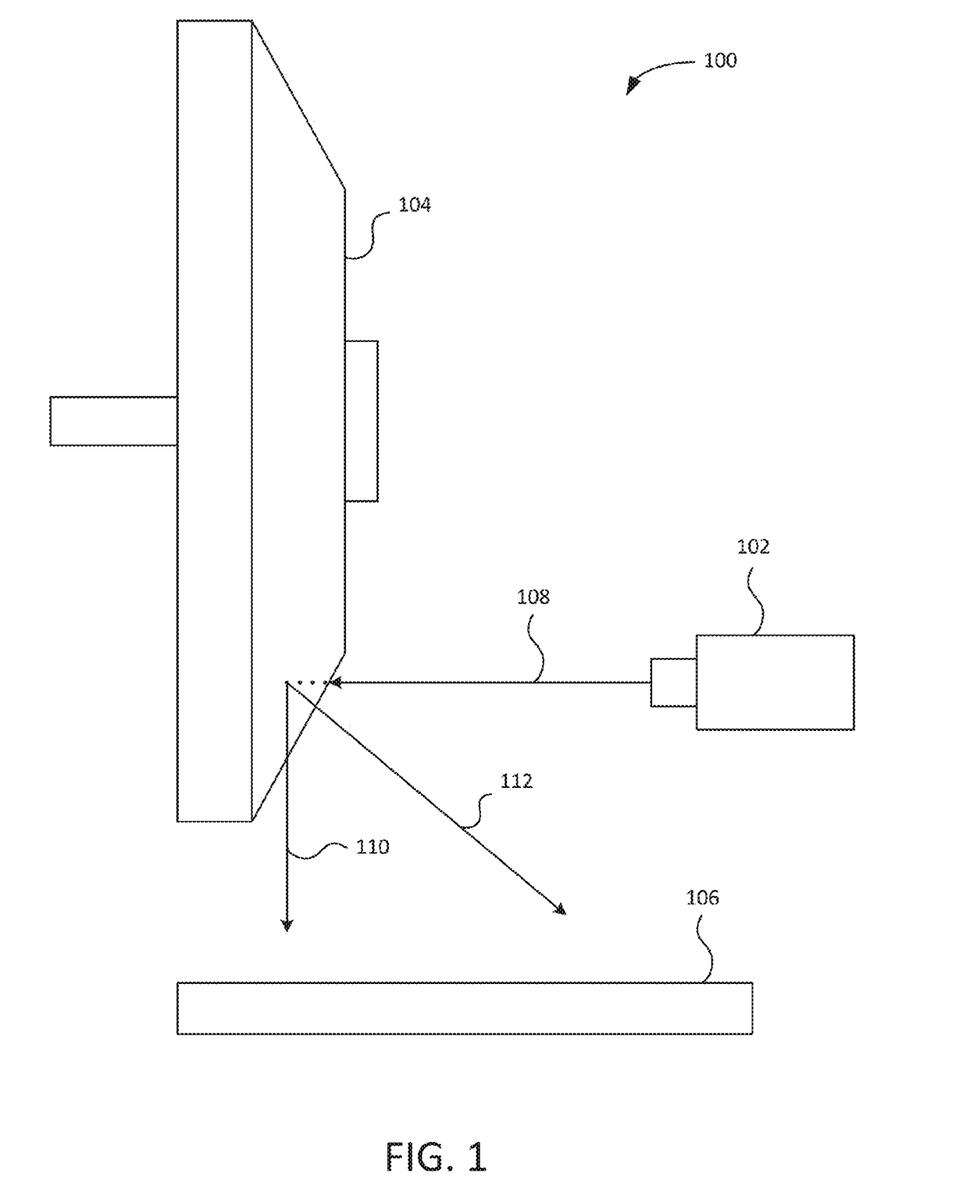
FIG. 1 illustrates an example x-ray imaging system that produces a heel effect.

FIG. 1 illustrates an example x-ray imaging system 100 that produces a heel effect. The x-ray imaging system 100 may include a cathode 102, an anode 104, and an x-ray detector 106. The cathode 102 may be configured to emit electrons via a thermionic emission process. The emitted electrons may be accelerated toward the anode 104 in an electron beam 108 by applying a high voltage potential difference between the cathode 102 and the anode 104. The electron beam 108 may strike the anode 104 and produce an x-ray beam, through either Bremsstrahlung or x-ray fluorescence processes, which may then be projected onto the x-ray detector 106. In some embodiments, the x-ray detector 106 may be a digital x-ray imager comprising multiple rows and/or columns of individual x-ray detectors that together may form x-ray images comprising multiple pixels. The voltage applied between the cathode 102 and the anode 104 may be varied to produce x-rays with different energy levels and wavelengths. For example, a 70 peak kilo-voltage (kVp) potential difference may be applied between the cathode 102 and anode 104 to produce x-rays at a first energy level and a 125 kVp potential difference may be applied between the cathode 102 and the anode 104 to produce x-rays at a second energy level. The x-rays produced at 70 kVp may have lower energy and greater wavelength than x-rays produced at 125 kVp.

The reduction in x-ray beam intensity toward the anode 104 side of the x-ray beam is referred to as the "heel effect." The heel effect is due to electrons that penetrate deep within the anode 104 material and produce x-rays. These x-rays must travel through more anode 104 material toward the anode 104 side of the x-ray beam in comparison to x-rays that are emitted toward the cathode 102 side of the x-ray beam. This process is illustrated in FIG. 1 by comparing a first x-ray 110 and a second x-ray 112 that are produced deep within the anode 104 material. The first x-ray 110 travels through the anode 104 material and exits the anode 104 toward the anode 104 side of the x-ray beam. The second x-ray 112 travels through the anode 104 material and exits the anode 104 toward the cathode 104 side of the x-ray beam. The first x-ray 110 must travel through more anode 104 material than the second x-ray 112 and is therefore more likely to be attenuated or absorbed by the anode 104 material. Thus, the overall x-ray beam intensity is proportionally lower toward the anode 104 side of the x-ray than the cathode 106 side of the x-ray beam.

Figure 2:
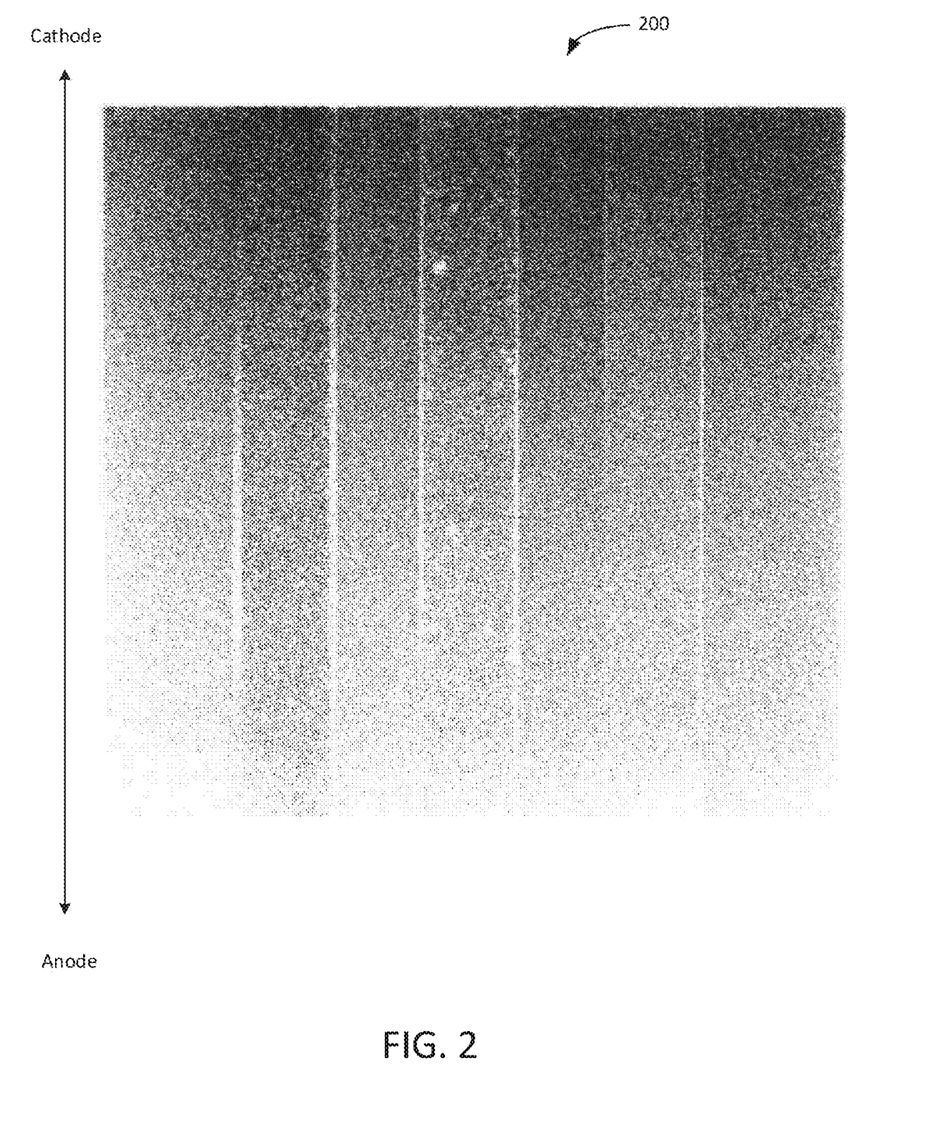
FIG. 2 is an example dual energy x-ray image illustrating distortion caused by the heel effect.

FIG. 2 illustrates an example dual energy x-ray image 200 that exhibits distortion caused by the heel effect. As illustrated in FIG. 2, the dual energy x-ray image 200 is more intense toward the cathode 106 side of the x-ray beam and less intense toward the anode 104 side of the x-ray beam. In general, dual energy x-ray images are composed of two x-ray images taken at different energy levels that are then combined to selectively enhance materials according to their atomic number. For example, soft tissue (low atomic number) may be enhanced by reducing the bone (high atomic number) in a dual energy x-ray image. The reverse may also be achieved to enhance the bone by reducing the soft tissue in a dual energy x-ray image.

FIG. 2 is one non-limiting example of a first x-ray image of a bone phantom (not shown) taken at 70 kVp and a second x-ray image of the bone phantom taken at 125 kVp. The first and second x-ray images were then mathematically combined by the following equation:

$$I_{DE}(i,j) = e^{\ln [I_H(i,j)] - W * \ln [I_L(i,j)]}; \quad\quad\quad (eq.\ 1)$$

where is $I_{DE}$ (i, j) is a resulting dual energy x-ray image calculated for each pixel in row i and column j; e is a mathematical constant≈2.71828 that is used as a base number in an exponential function; the function ln [ ] is a natural logarithm function; $I_H$ (i, j) is the second x-ray image taken at a higher kVp (in this example, 125 kVp); W is a weight factor that may range between zero and one, in at least some embodiments; and $I_L$ (i, j) is the first x-ray image taken at a lower kVp (in this example, 70 kVp). When this algorithm is applied to the first and second x-ray images of this example with a weight factor W of≈0.6, the bones are reduced in intensity and the soft tissue is enhanced, as may be seen in FIG. 2. However, as noted previously the dual energy x-ray image 200 exhibits distortion caused by the heel effect.

Heel effect distortion may be reduced or eliminated from dual energy x-ray images by applying one or more additional calibration images to normalize differences in x-ray beam intensity uniformity due to heel effects that occur at different x-ray energy levels. For example, in one embodiment, two flood field images may be taken with no objects between the anode 104 and the x-ray detector 106 at the same x-ray energy levels as the first and second x-ray images, corresponding to a low energy level and a high energy level respectively. A normalize image may then be formed by combining the two flood field images according to the equation:

$$I_N(i,j)=[FF_H(i,j)/FF_L(i,j)]/\text{MEAN}([FF_H(i,j)/FF_L(i,j)]); \quad (\text{eq. 2})$$

where $I_N$ (i, j) is the normalize image; $FF_H$ (i, j) is a flood field image taken at the higher x-ray energy level; $FF_L$ (i, j) is a flood field image taken at the lower x-ray energy level; and the function MEAN( ) is a function that denotes taking the mean or average value of pixels of an image input into the function. The expression $[FF_H$ (i, j)/$FF_L$ (i, j)] may also be referred to as an intermediate image. In this embodiment, the normalize image $I_N$ (i, j) may be applied to the second x-ray image in the dual energy calculation equation to normalize out differences in x-ray beam intensity uniformity due to heel effects which occur at different x-ray energy levels, as follows:

$$I_{DE}(i,j)=e^{\ln{[I_H(i,j)*I_N(i,j)]}-W*\ln{[I_L(i,j)]}}; \quad (\text{eq. 3})$$

Figure 7:
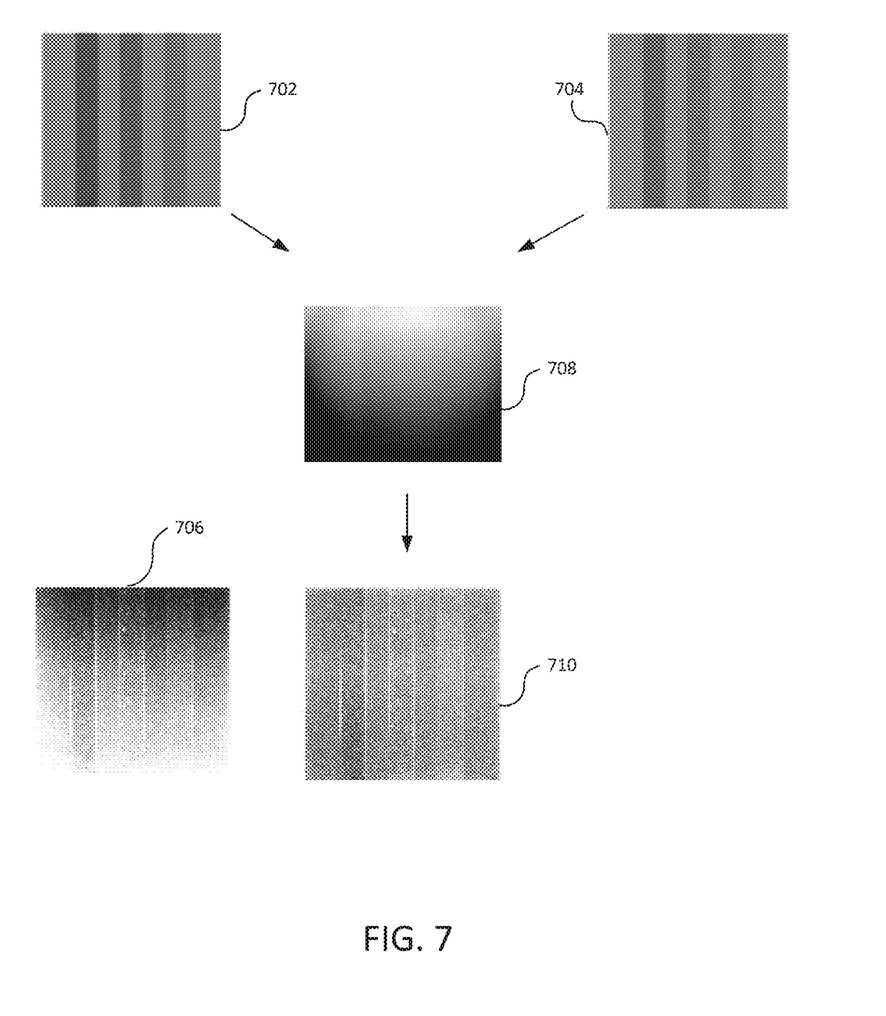
FIG. 7 illustrates various example x-ray images.

FIG. 7 illustrates how the dual energy x-ray image 200 of FIG. 2 may be normalized by the processes discussed above to reduce or eliminate distortion caused by the heel effect. A first x-ray image 702 and a second x-ray image 704 may be generated by x-rays at first and second energy levels, respectively. Where the first and second x-ray images 702, 704 are combined together using equation 1 above with a weighting factor W of≈0.6, the resulting dual energy x-ray image 706 may include heel effect distortion. The dual energy x-ray image 706 corresponds to the dual energy x-ray image 200 of FIG. 2.

Conversely, in some embodiments, a normalize image 708 may be calculated. For example, the normalized image 708 may be calculated using equation 2. The normalized image 708 may be used in conjunction with equation 3 with a weighting factor W of≈0.6 to generate a dual energy x-ray image 710 having little or no heel effect distortion, as can be seen in comparisons of the dual energy x-ray image 706 and the dual energy x-ray image 710.

In another embodiment, three flood field images may be taken with no objects between the anode 104 and the x-ray detector 106. Two of the flood field images may be taken at the same x-ray energy levels as the first and second x-ray images, corresponding to a low energy level and a high energy level respectively, and the third flood field image may be taken at an arbitrary x-ray energy level. In some embodiments, the third flood field image may correspond to a calibration image acquired at a calibration x-ray energy level. First and second normalize images may then be formed by combining the three flood field images according to the following equations:

$$I_{N1}(i,j)=[FF_L(i,j)/FF_A(i,j)]/\text{MEAN}([FF_L(i,j)/FF_A(i,j)]); \quad (\text{eq. 4})$$

$$I_{N2}(i,j)=[FF_H(i,j)/FF_A(i,j)]/\text{MEAN}([FF_H(i,j)/FF_A(i,j)]); \quad (\text{eq. 5})$$

where $I_{N1}$ (i, j) is the first normalize image; $FF_L$ (i, j) is the flood field image taken at the lower x-ray energy level; $FF_A$ (i, j) is the flood field image taken at the arbitrary x-ray energy level; $FF_H$ (i, j) is the flood field image taken at the higher x-ray energy level; and the function MEAN( ) is a function that denotes taking the mean or average value of pixels of an image input into the function. The expressions $[FF_L$ (i, j)/$FF_A$ (i, j)] and $[FF_H$ (i, j)/$FF_A$ (i, j)] may be referred to as a first intermediate image and a second intermediate image, respectively. In this embodiment, the first and second normalize images $I_{N1}$ (i, j), $I_{N2}$ (i, j) may be applied to the first and second x-ray images to normalize out differences in x-ray beam intensity uniformity due to heel effects which occur at different x-ray energy levels, as follows:

$$I_{DE}(i,j)=e^{\ln{[I_H(i,j)*I_{N2}(i,j)]}-W*\ln{[I_L(i,j)*I_{N1}(i,j)]}}; \quad (\text{eq. 6})$$

Figure 3:
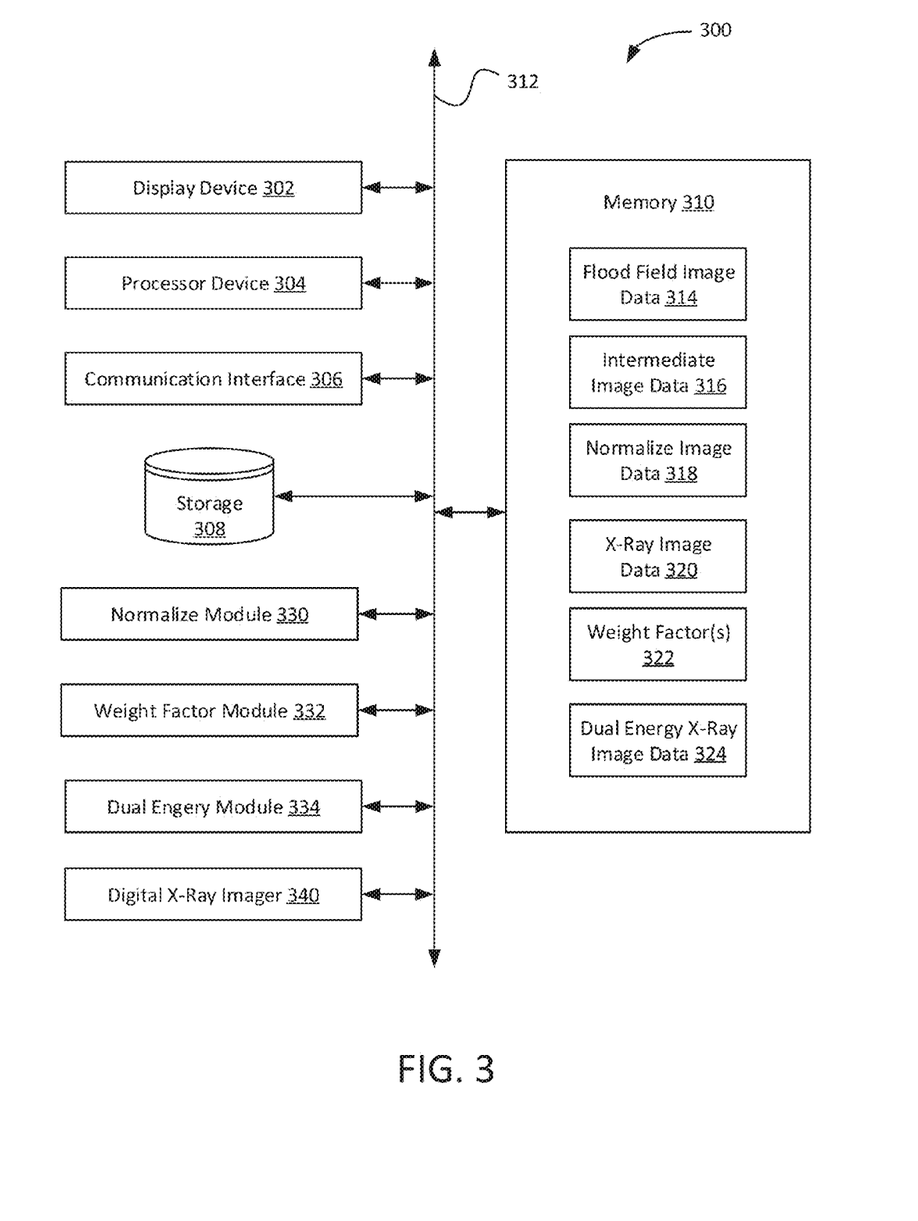
FIG. 3 is a block diagram illustrating an example system to reduce heel effect in dual energy x-ray images.

FIG. 3 is a block diagram illustrating an example system 300 to reduce heel effect in dual energy x-ray images, arranged in accordance with at least some embodiments described herein. The system 300 may be implemented as a computing device having any suitable form factor, such as a computing device associated with an x-ray imaging system, a desktop computer, a laptop, a tablet device, or other suitable computing device. The system 300 may include a display device 302. The display device 302 may be configured to display x-ray images, instructions, or other information to a user (not shown). The system 300 may also include a processor device 304, a communication interface 306, a storage 308, a memory 310, a normalize module 330, a weight factor module 332, a dual energy module 334 (collectively referred to herein as "modules"), and a digital x-ray imager 340, according to some examples. The digital x-ray imager 340 may correspond to the x-ray detector 106 of FIG. 1 in at least some embodiments. The components of the system 300 may be communicatively coupled by a bus 312. The bus 312 may include one or more of a memory bus, a storage interface bus, a bus/interface controller, an interface bus, or other suitable bus.

The processor device 304 can include an arithmetic logic unit, a microprocessor, a general-purpose controller, or some other processor or processor array to perform or control performance of operations as described herein. The processor device 304 processes data signals and may include various computing architectures including a complex instruction set computer (CISC) architecture, a reduced instruction set computer (RISC) architecture, or an architecture implementing a combination of instruction sets. Although FIG. 3 includes a single processor device 304, multiple processor devices may be included. Other processors, operating systems, and physical configurations may be possible.

The communication interface 306 may be configured to receive and/or transmit data to and from the digital x-ray imager 340 and/or other computing devices (not shown). In some implementations, the communication interface 306 includes a port for direct physical connection to the digital x-ray imager 340 or to another communication channel associated with other computing devices. For example, the communication interface 306 may include a universal serial bus (USB) port, a secure digital (SD) port, a category 5 cable (CAT-5) port, or similar port for wired communication with the digital x-ray imager 340 or other computing devices. The communication interface 306 may also provide other connections to a network (not shown) for data communication using standard network protocols including transmission control protocol/internet protocol (TCP/IP), HTTP, HTTP secure (HTTPS), and simple mail transfer protocol (SMTP), etc. In some implementations, the communication interface 306 may include a wireless transceiver (not shown) for exchanging data with the digital x-ray imager 340 or other communication channels. In these and other embodiments, the transceiver may use one or more wireless communication methods, including IEEE 802.11, IEEE 802.16, Bluetooth®, Bluetooth Low Energy®, Bluetooth SMART®, Wi-Fi, cellular, Near Field communications, ZigBee, or any other suitable wireless communication method to communicate with the digital x-ray imager 340 or other computing devices.

The storage 308 may include a non-transitory storage medium that stores instructions and/or data for providing the functionality described herein. The storage 308 may include a dynamic random access memory (DRAM) device, a static random access memory (SRAM) device, flash memory, or some other memory devices. In some implementations, the storage 308 also includes a non-volatile memory or similar permanent storage and media including a hard disk drive, a floppy disk drive, a CD-ROM device, a DVD-ROM device, a DVD-RAM device, a DVD-RW device, a flash memory device, or some other mass storage for storing information on a more permanent basis. The storage 308 may also store instructions and/or data that are temporarily stored or loaded into the memory 310.

The memory 310 may store instructions or data that may be executed or operated on by the processor device 304. The instructions or data may include programming code that may be executed by the processor device 304 to perform or control performance of the operations described herein. The memory 310 may include a dynamic random access memory (DRAM) device, a static random access memory (SRAM) device, flash memory, or some other memory device. In some implementations, the memory 310 may include a non-volatile memory or similar permanent storage and media including a hard disk drive, a floppy disk drive, a CD-ROM device, a DVD-ROM device, a DVD-RAM device, a DVD-RW device, a flash memory device, or some other mass storage for storing information on a more permanent basis. The memory 310 and/or storage 308 may store data including, but not limited to, flood field image data 314, intermediate image data 316, normalize image data 318, x-ray image data 320, one or more weight factors 322, and dual energy x-ray image data 324.

The modules 330, 332, 334, may generally include software that includes programming code and/or computer-readable instructions executable by the processor device 304 to perform or control performance of the functions and operations described herein. The modules 330, 332, 334, may receive data from each other or from another one of the components of the system 300 and may store data in one or both of the storage 308 and the memory 310. The normalize module 330 may generally be configured to generate one or more normalize images based on two or more flood field images. The weight factor module 332 may generally be configured to manage and/or apply one or more weight factors 322 during dual energy x-ray image calculations. The dual energy module 334 may generally be configured to generate dual energy x-ray images.

An example implementation of the system 300 will now be discussed with reference to FIGS. 1 and 3. A first flood field image may be generated by the x-ray imaging system of FIG. 1 at a first x-ray energy level with no objects between the anode 104 and the x-ray detector 106. The x-ray detector 106 may be a digital x-ray imager 340, as previously discussed. The digital x-ray imager 340 may digitally capture and communicate the first flood field image to the system 300 where the first flood field image may be stored as flood field image data 314 in the memory 310. A second flood field image may be generated by the x-ray imaging system of FIG. 1 at a second x-ray energy level with no objects between the anode 104 and the digital x-ray imager 340. The digital x-ray imager 340 may digitally capture and communicate the second flood field image to the system 300 where the second flood field image may be stored as flood field image data 314 in the memory 310. The x-rays at the first energy level may be generated with a lower energy level than the x-rays at the second energy level.

The normalize module 330 may be configured to access the flood image data 314 from the memory 310 or receive the flood image data 314 from the digital x-ray imager 340 and generate a normalize image based on the first flood field image and the second flood field image. The normalize module 330 may be configured to generate an intermediate image by dividing the second flood field image by the first flood field image and store the intermediate image in the memory 310 as intermediate image data 316. The normalize module 330 may also be configured to calculate a mean of the intermediate image and divide the intermediate image by the mean of the intermediate image to generate the normalize image. The normalize module 330 may store the normalize image in the memory 310 as normalize image data 318.

A first x-ray image may be generated by the x-ray imaging system of FIG. 1 at the first x-ray energy level with the desired object between the anode 104 and the x-ray detector 106 or digital x-ray imager 340. The digital x-ray imager 340 may digitally capture and communicate the first x-ray image to the system 300 where the first x-ray image may be stored as x-ray image data 320 in the memory 310. A second x-ray image may be generated by the x-ray imaging system of FIG. 1 at the second x-ray energy level with the desired object between the anode 104 and the digital x-ray imager 340. The digital x-ray imager 340 may digitally capture and communicate the second x-ray image to the system 300 where the second x-ray image may be stored as x-ray image data 320 in the memory 310.

The weight factor module may be configured to receive, store, and/or access one or more desired weight factors 322 for application to dual energy x-ray image calculations. In at least some embodiments, the one or more desired weight factors 322 may include a number between zero and one and may be selected to enhance or reduce x-ray images of different materials according to their specific atomic numbers.

The dual energy module 334 may be configured to receive the first and second x-ray images stored as x-ray image data 320 in the memory 310, or directly from the digital x-ray imager 340. The dual energy module 334 may be configured to apply the normalize image to the second x-ray image to generate a normalized second x-ray image and then combine the first x-ray image with the normalized second x-ray image to generate a dual energy x-ray image, according to equation 3 above. The dual energy module 334 may also be configured to store the dual energy x-ray image as dual energy x-ray image data 234 in the memory 310.

An alternative example implementation of the system 300 will now be discussed with reference to FIGS. 1 and 3. A first flood field image may be generated by the x-ray imaging system of FIG. 1 at a first x-ray energy level with no objects between the anode 104 and the x-ray detector 106, or digital x-ray imager 340. The digital x-ray imager 340 may digitally capture and communicate the first flood field image to the system 300 where the first flood field image may be stored as flood field image data 314 in the memory 310. A second flood field image may be generated by the x-ray imaging system of FIG. 1 at a second x-ray energy level with no objects between the anode 104 and the digital x-ray imager 340. The digital x-ray imager 340 may digitally capture and communicate the second flood field image to the system 300 where the second flood field image may be stored as flood field image data 314 in the memory 310. A third flood field image may be generated by the x-ray imaging system of FIG. 1 at a third x-ray energy level with no objects between the anode 104 and the digital x-ray imager 340. The digital x-ray imager 340 may digitally capture and communicate the third flood field image to the system 300 where the third flood field image may be stored as flood field image data 314 in the memory 310. The x-rays at the first energy level may be generated with a lower energy level than the x-rays at the second energy level and the x-rays at the third energy level may be generated at an arbitrary energy level.

The normalize module 330 may be configured to access the flood image data 314 from the memory 310 or receive the flood image data 314 from the digital x-ray imager 340 and generate first and second normalize images based on the first, second, and third flood field images. The normalize module 330 may also be configured to generate first and second intermediate images. The first intermediate image may be generated by dividing the first flood field image by the third flood field image. The normalize module 330 may also be configured to calculate a mean of the first intermediate image and divide the first intermediate image by the mean of the first intermediate image to generate the first normalize image. The second intermediate image may be generated by dividing the second flood field image by the third flood field image. The normalize module 330 may also be configured to calculate a mean of the second intermediate image and divide the second intermediate image by the mean of the second intermediate image to generate the second normalize image. The normalize module 330 may also be configured to store the first and second intermediate images in the memory 310 as intermediate image data 316 and store the first and second normalize images in the memory 310 as normalize image data 318.

A first x-ray image may be generated by the x-ray imaging system of FIG. 1 at the first x-ray energy level with the desired object between the anode 104 and the x-ray detector 106, or digital x-ray imager 340. The digital x-ray imager 340 may digitally capture and communicate the first x-ray image to the system 300 where the first x-ray image may be stored as x-ray image data 320 in the memory 310. A second x-ray image may be generated by the x-ray imaging system of FIG. 1 at the second x-ray energy level with the desired object between the anode 104 and the digital x-ray imager 340. The digital x-ray imager 340 may digitally capture and communicate the second x-ray image to the system 300 where the second x-ray image may be stored as x-ray image data 320 in the memory 310.

The dual energy module 334 may be configured to receive the first and second x-ray images stored as x-ray image data 320 in the memory 310, or directly from the digital x-ray imager 340. The dual energy module 334 may be configured to apply the first and second normalize images to the first and second x-ray images to generate normalized first and second x-ray images and then combine the first and second normalized x-ray images to generate a dual energy x-ray image, according to equation 6 above. The dual energy module 334 may also be configured to store the dual energy x-ray image as dual energy x-ray image data 234 in the memory 310.

Figure 4:
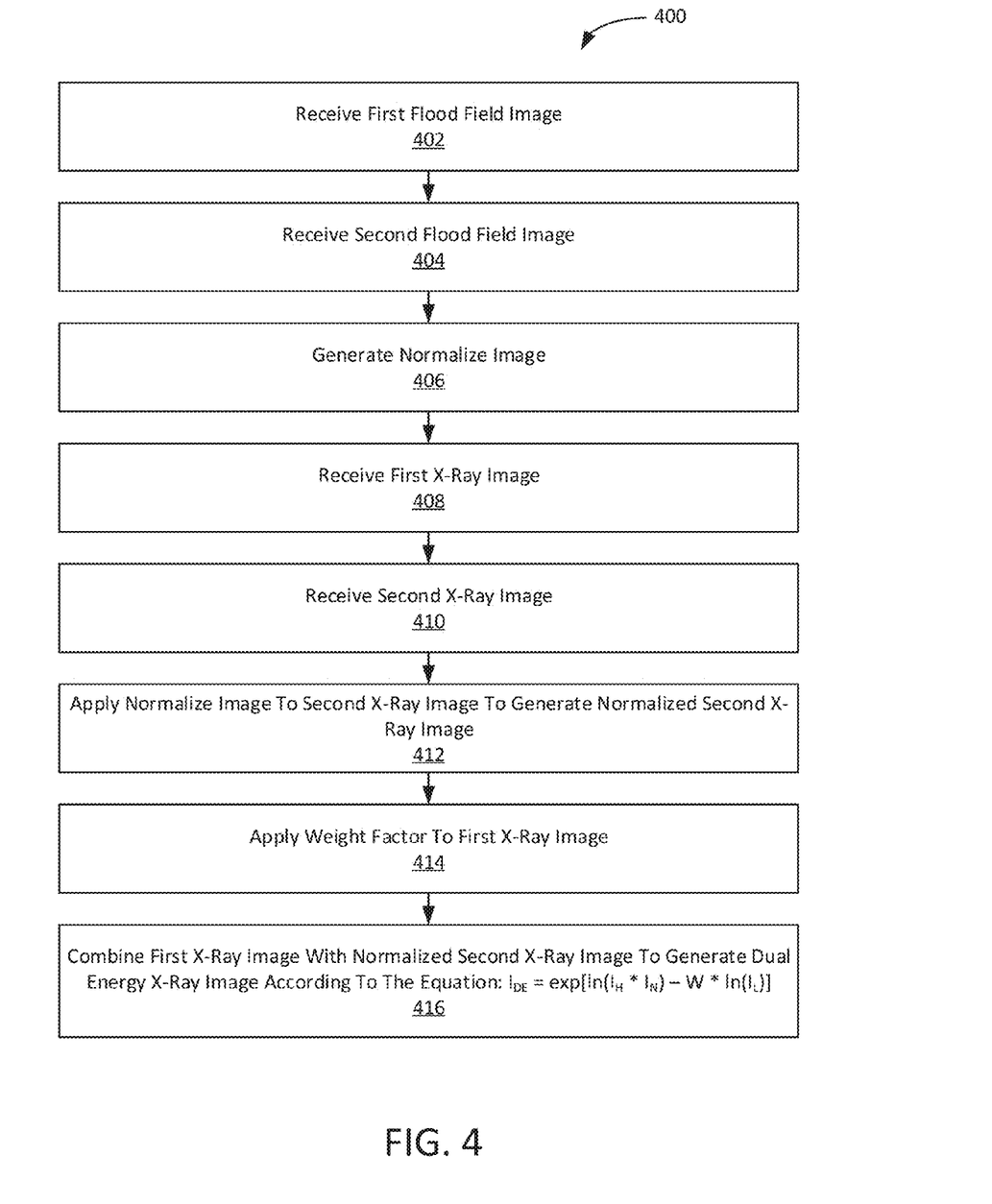
FIG. 4 is an example flow diagram illustrating a method to generate dual energy x-ray images with reduced heel effect.

FIG. 4 shows a flow diagram of an example method 400 to generate dual energy x-ray images with reduced heel effect, arranged in accordance with at least some embodiments described herein. The method 400 may be implemented, in whole or in part, by the system 300 of FIG. 3, or another suitable device or system. The method 400 may begin at block 402.

In block 402 ("Receive First Flood Field Image"), a first flood image may be received. The first flood image may be generated by x-rays at a first energy level without any object between the x-ray source and the x-ray detector. Block 402 may be followed by block 404.

In block 404 ("Receive Second Flood Field Image"), a second flood image may be received. The second flood image may be generated by x-rays at a second energy level without any object between the x-ray source and the x-ray detector. The x-rays at the first energy level may have a lower energy level than the x-rays at the second energy level. Block 404 may be followed by block 406.

In block 406 ("Generate Normalize Image"), a normalize image may be generated based on the first flood field image and the second flood field image. The second flood field image may be divided by the first flood field image to generate an intermediate image. A mean of the intermediate image may be calculated and the intermediate image may be divided by the mean of the intermediate image to generate the normalize image. Block 406 may be followed by block 408.

In block 408 ("Receive First X-Ray Image"), a first x-ray image may be received. The first x-ray image may be generated by x-rays at the first energy level with a desired object between the x-ray source and the x-ray detector. Block 408 may be followed by block 410.

In block 410 ("Receive Second X-Ray Image"), a second x-ray image may be received. The second x-ray image may be generated by x-rays at the second energy level with the desired object between the x-ray source and the x-ray detector. Block 410 may be followed by block 412.

In block 412 ("Apply Normalize Image To Second X-Ray Image To Generate Normalized Second X-Ray Image"), the normalize image may be applied to the second x-ray image to generate a normalized second x-ray image. The normalize image may be applied to the second x-ray image by multiplying corresponding pixels of the normalize image and the second x-ray image with each other. Block 412 may be followed by block 414.

In block 414 ("Apply Weight Factor To First X-Ray Image"), a weight factor 322 may be applied to the first x-ray image. In some embodiments, the weight factor 322 comprises a number between zero and one. The weight factor 322 may be applied to the natural logarithm of the first x-ray image by multiplying the natural logarithm of each pixel of the first x-ray image by the weight factor 322. Block may be 414 may be followed by block 416.

In block 416 ("Combine First X-Ray Image With Normalized Second X-Ray Image To Generate Dual Energy X-Ray Image According To The Equation: $I_{DE}=\exp[\ln(I_H*I_N)-W*\ln(I_L)]$"), the first x-ray image may be combined with the normalized second x-ray image to generate a dual energy x-ray image calculated according to $I_{DE}=\exp[\ln(I_H*I_N)-W*\ln(I_L)]$, where $I_{DE}$ is the dual energy x-ray image, exp is an exponential function, ln is a natural logarithm function, $I_H$ is the second x-ray image, $I_N$ is the normalize image, W is the weight factor, and $I_L$ is the first x-ray image.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed implementations.

Figure 5:
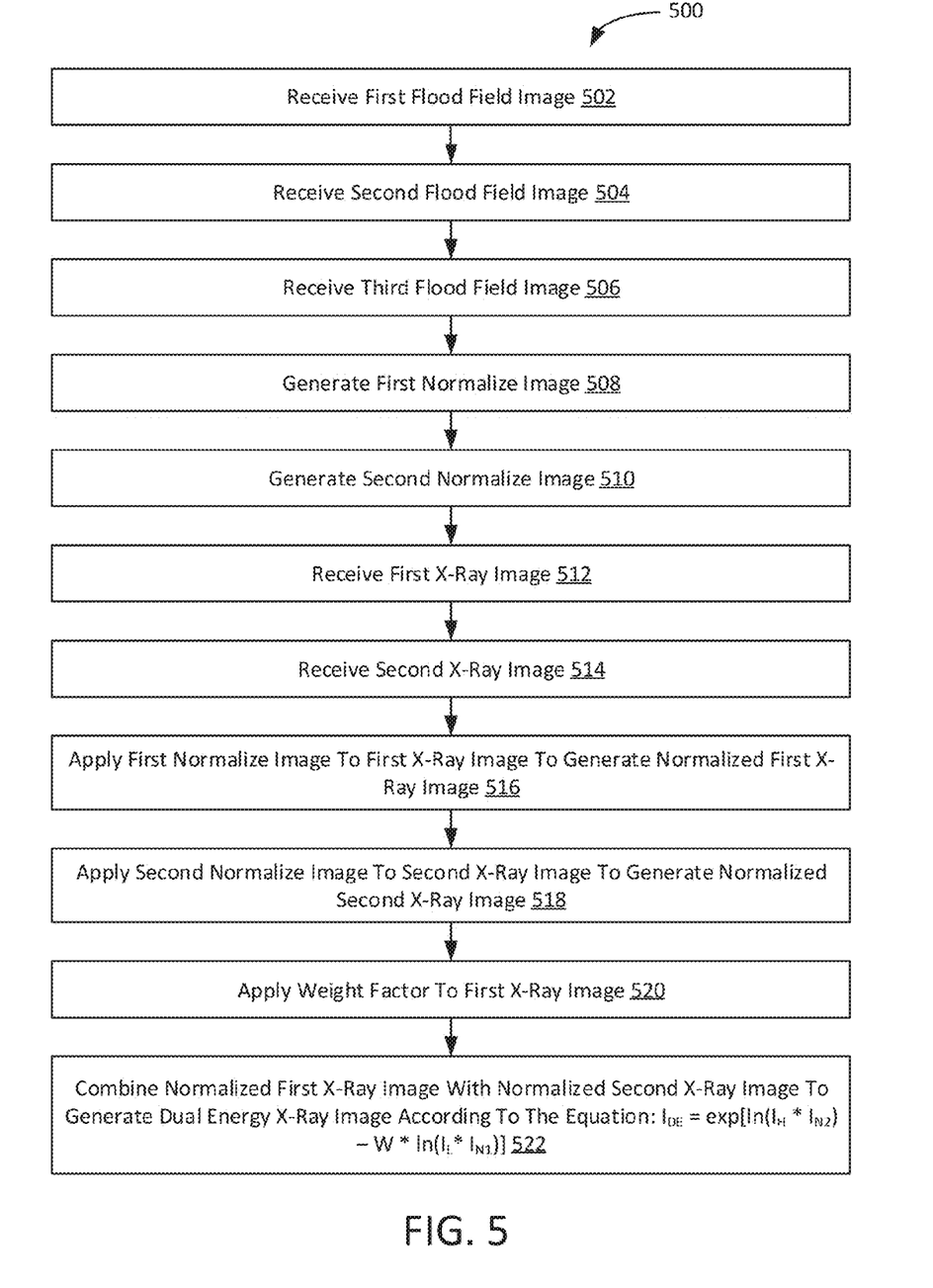
FIG. 5 is an example flow diagram illustrating an alternative method to generate dual energy x-ray images with reduced heel effect.

FIG. 5 shows a flow diagram of an example method 500 to generate dual energy x-ray images with reduced heel effect, arranged in accordance with at least some embodiments described herein. The method 500 may be implemented, in whole or in part, by the system 300 of FIG. 3, or another suitable device or system. The method 500 may begin at block 502.

In block 502 ("Receive First Flood Field Image"), a first flood image may be received. The first flood image may be generated by x-rays at a first energy level without any object between the x-ray source and the x-ray detector. Block 502 may be followed by block 504.

In block 504 ("Receive Second Flood Field Image"), a second flood image may be received. The second flood image may be generated by x-rays at a second energy level without any object between the x-ray source and the x-ray detector. The x-rays at the first energy level may have a lower energy level than the x-rays at the second energy level. Block 504 may be followed by block 506.

In block 506 ("Receive Third Flood Field Image"), a third flood image may be received. The third flood image may be generated by x-rays at a third energy level without any object between the x-ray source and the x-ray detector. The x-rays at the third energy level may be generated at an arbitrary energy level. Block 506 may be followed by block 508.

In block 508 ("Generate First Normalize Image"), a first normalize image may be generated based on the first flood field image and the third flood field image. The first flood field image may be divided by the third flood field image to generate a first intermediate image. A mean of the first intermediate image may be calculated and the first intermediate image may be divided by the mean of the first intermediate image to generate the first normalize image. Block 508 may be followed by block 510.

In block 510 ("Generate Second Normalize Image"), a second normalize image may be generated based on the second flood field image and the third flood field image. The second flood field image may be divided by the third flood field image to generate a second intermediate image. A mean of the second intermediate image may be calculated and the second intermediate image may be divided by the mean of the second intermediate image to generate the second normalize image. Block 510 may be followed by block 512.

In block 512 ("Receive First X-Ray Image"), a first x-ray image may be received. The first x-ray image may be generated by x-rays at the first energy level with a desired object between the x-ray source and the x-ray detector. Block 512 may be followed by block 514.

In block 514 ("Receive Second X-Ray Image"), a second x-ray image may be received. The second x-ray image may be generated by x-rays at the second energy level with the desired object between the x-ray source and the x-ray detector. Block 514 may be followed by block 516.

In block 516 ("Apply First Normalize Image To First X-Ray Image To Generate Normalized First X-Ray Image"), the first normalize image may be applied to the first x-ray image to generate a normalized first x-ray image. The first normalize image may be applied to the first x-ray image by multiplying corresponding pixels of the first normalize image and the first x-ray image with each other. Block 516 may be followed by block 518.

In block 518 ("Apply Second Normalize Image To Second X-Ray Image To Generate Normalized Second X-Ray Image"), the second normalize image may be applied to the second x-ray image to generate a normalized second x-ray image. The second normalize image may be applied to the second x-ray image by multiplying corresponding pixels of the second normalize image and the second x-ray image with each other. Block 518 may be followed by block 520.

In block 520 ("Apply Weight Factor To First X-Ray Image"), a weight factor 322 may be applied to the first x-ray image. In some embodiments, the weight factor 322 comprises a number between zero and one. The weight factor 322 may be applied to the natural logarithm of the first x-ray image multiplied by the first normalize image. Block 520 may be followed by block 522.

In block 522 ("Combine Normalized First X-Ray Image With Normalized Second X-Ray Image To Generate Dual Energy X-Ray Image According To The Equation: $I_{DE}=\exp[\ln(I_H*I_{N2})-W*\ln(I_L*I_{N1})]$,") the normalized first x-ray image may be combined with the normalized second x-ray image to generate a dual energy x-ray image calculated according to $I_{DE}=\exp[\ln(I_H*I_{N2})-W*\ln(I_L*I_{N1})]$, where is $I_{DE}$ is the dual energy x-ray image, exp is an exponential function, ln is a natural logarithm function, $I_H$ is the second x-ray image, $I_{N2}$ is the second normalize image, W is the weight factor, $I_L$ is the first x-ray image, and $I_{N1}$ is the first normalize image.

Figure 6A:
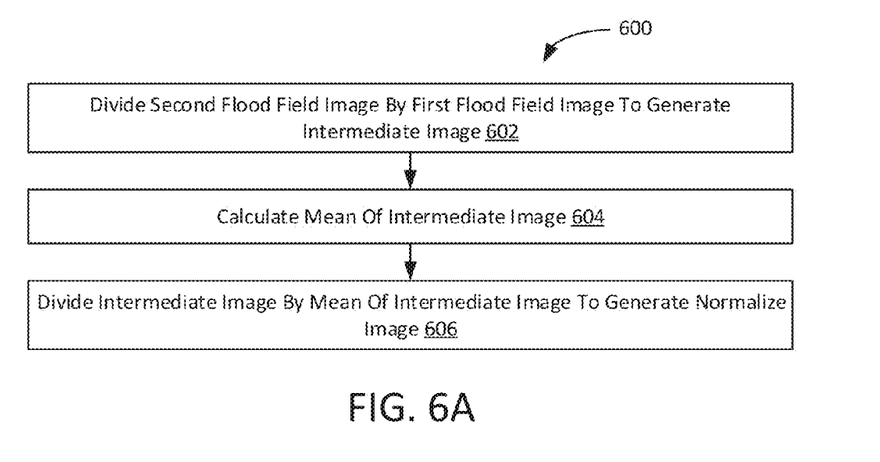
FIG. 6A is an example flow diagram illustrating a method to generate a normalize image that may be used in the method of FIG. 4.

FIG. 6A shows a flow diagram of an example method 600 to generate a normalize image that may be used in the method of FIG. 4, arranged in accordance with at least some embodiments described herein. The method 600 may be implemented, in whole or in part, by the system 300 of FIG. 3, or another suitable device or system. The method 600 may begin at block 602.

In block 602 ("Divide Second Flood Field Image By First Flood Field Image To Generate Intermediate Image"), the second flood field image may be divided by the first flood field image to generate an intermediate image. Block 602 may be followed by block 604.

In block 604 ("Calculate Mean Of Intermediate Image"), A mean of the intermediate image may be calculated. Block 604 may be followed by block 606.

In block 606 ("Divide Intermediate Image By Mean Of Intermediate Image To Generate Normalize Image"), The intermediate image may be divided by the mean of the intermediate image to generate the normalize image.

Figure 6B:
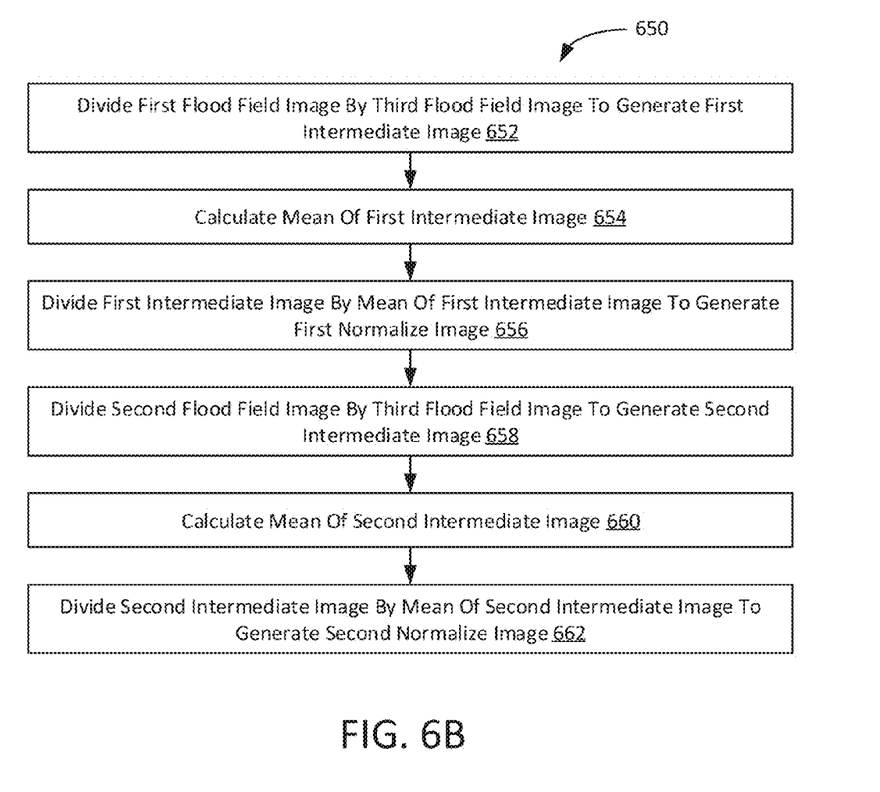
FIG. 6B is an example flow diagram illustrating an alternative method to generate normalize images that may be used in the method of FIG. 5.

FIG. 6B shows a flow diagram of an example alternative method 650 to generate normalize images that may be used in the method of FIG. 5, arranged in accordance with at least some embodiments described herein. The method 650 may be implemented, in whole or in part, by the system 300 of FIG. 3, or another suitable device or system. The method 650 may begin at block 652.

In block 652 ("Divide First Flood Field Image By Third Flood Field Image To Generate First Intermediate Image"), the first flood field image may be divided by the third flood field image to generate a first intermediate image. Block 652 may be followed by block 654.

In block 654 ("Calculate Mean Of First Intermediate Image"), a mean of the first intermediate image may be calculated. Block 654 may be followed by block 656.

In block 656 ("Divide First Intermediate Image By Mean Of First Intermediate Image To Generate First Normalize Image"), the first intermediate image may be divided by the mean of the first intermediate image to generate the first normalize image. Block 656 may be followed by block 658.

In block 658 ("Divide Second Flood Field Image By Third Flood Field Image To Generate Second Intermediate Image"), the second flood field image may be divided by the third flood field image to generate a second intermediate image. Block 658 may be followed by block 660.

In block 660 ("Calculate Mean Of Second Intermediate Image"), a mean of the second intermediate image may be calculated. Block 660 may be followed by block 662.

In block 662 ("Divide Second Intermediate Image By Mean Of Second Intermediate Image To Generate Second Normalize Image"), the second intermediate image may be divided by the mean of the second intermediate image to generate the second normalize image.

The implementations described herein may include the use of a special purpose or general-purpose computer including various computer hardware or software modules, as discussed in greater detail below.

Embodiments within the scope of the technology disclosed herein may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above may also be included within the scope of computer-readable media.

Computer-executable instructions comprise, for example, instructions and data that cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The present disclosure is not to be limited in terms of the particular embodiments described herein, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting. Accordingly, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for reducing heel effect distortion in dual energy x-ray images, the method comprising:
   receiving a first flood field image generated by x-rays at a first energy level;
   receiving a second flood field image generated by x-rays at a second energy level;
   generating a normalize image based on the first flood field image and the second flood field image;
   receiving a first x-ray image generated by x-rays at the first energy level;
   receiving a second x-ray image generated by x-rays at the second energy level;
   applying the normalize image to the second x-ray image to generate a normalized second x-ray image; and
   combining the first x-ray image with the normalized second x-ray image to generate a dual energy x-ray image.

2. The method of claim 1, wherein the x-rays at the first energy level have a lower energy level than the x-rays at the second energy level.

3. The method of claim 2, wherein generating the normalize image based on the first flood field image and the second flood field image further comprises:
   dividing the second flood field image by the first flood field image to generate an intermediate image;
   calculating a mean of the intermediate image; and
   dividing the intermediate image by the mean of the intermediate image to generate the normalize image.

4. The method of claim 3, further comprising applying a weight factor to the first x-ray image, the weight factor comprising a number between zero and one.

5. The method of claim 4, wherein combining the first x-ray image with the normalized second x-ray image to generate the dual energy x-ray image is calculated according to $I_{DE}=\exp[\ln(I_H * I_N) - W * \ln(I_L)]$, where $I_{DE}$ is the dual energy x-ray image, exp is an exponential function, ln is a natural logarithm function, $I_H$ is the second x-ray image, $I_N$ is the normalize image, W is the weight factor, and $I_L$ is the first x-ray image.

6. A system for reducing heel effect distortion in dual energy x-ray images, the system comprising:
   a normalize module configured to:
      receive a first flood field image generated by x-rays at a first energy level;
      receive a second flood field image generated by x-rays at a second energy level; and
      generate a normalize image based on the first flood field image and the second flood field image; and
   a dual energy module configured to:
      receive a first x-ray image generated by x-rays at the first energy level;
      receive a second x-ray image generated by x-rays at the second energy level;
      apply the normalize image to the second x-ray image to generate a normalized second x-ray image; and
      combine the first x-ray image with the normalized second x-ray image to generate a dual energy x-ray image.

7. The system of claim 6, wherein the x-rays at the first energy level have a lower energy level than the x-rays at the second energy level.

8. The system of claim 7, wherein the normalize module is further configured to:
   divide the second flood field image by the first flood field image to generate an intermediate image;
   calculate a mean of the intermediate image; and
   divide the intermediate image by the mean of the intermediate image to generate the normalize image.

9. The system of claim 8, further comprising a weight factor module configured to apply a weight factor to the first x-ray image, the weight factor comprising a number between zero and one.

10. The system of claim 9, wherein the dual energy module is configured to combine the first x-ray image with the normalized second x-ray image to generate the dual energy x-ray image according to $I_{DE}=\exp[\ln(I_H * I_N) - W * \ln(I_L)]$, where is $I_{DE}$ is the dual energy x-ray image, exp is an exponential function, ln is a natural logarithm function, $I_H$ is the second x-ray image, $I_N$ is the normalize image, W is the weight factor, and $I_L$ is the first x-ray image.

11. A non-transitory computer-readable medium that includes computer-readable instructions stored thereon that are executable by a processor to perform or control performance of operations, the operations comprising:
   receiving a first flood field image generated by x-rays at a first energy level;
   receiving a second flood field image generated by x-rays at a second energy level;
   generating a normalize image based on the first flood field image and the second flood field image;
   receiving a first x-ray image generated by x-rays at the first energy level;
   receiving a second x-ray image generated by x-rays at the second energy level;
   applying the normalize image to the second x-ray image to generate a normalized second x-ray image; and combining the first x-ray image with the normalized second x-ray image to generate a dual energy x-ray image.

12. The non-transitory computer-readable medium of claim 11, wherein the x-rays at the first energy level have a lower energy level than the x-rays at the second energy level.

13. The non-transitory computer-readable medium of claim 12, wherein generating the normalize image based on the first flood field image and the second flood field image further comprises:
dividing the second flood field image by the first flood field image to generate an intermediate image;
calculating a mean of the intermediate image; and
dividing the intermediate image by the mean of the intermediate image to generate the normalize image.

14. The non-transitory computer-readable medium of claim 13, wherein the operations further comprise applying a weight factor to the first x-ray image, the weight factor comprising a number between zero and one.

15. The non-transitory computer-readable medium of claim 14, wherein combining the first x-ray image with the normalized second x-ray image to generate the dual energy x-ray image is calculated according to $I_{DE}=\exp[\ln(I_H*I_N)-W*\ln(I_L)]$, where is $I_{DE}$ is the dual energy x-ray image, exp is an exponential function, ln is a natural logarithm function, $I_H$ is the second x-ray image, $I_N$ is the normalize image, W is the weight factor, and $I_L$ is the first x-ray image.

16. A method for reducing heel effect distortion in dual energy x-ray images, the method comprising:
receiving a first flood field image generated by x-rays at a first energy level;
receiving a second flood field image generated by x-rays at a second energy level;
receiving a third flood field image generated by x-rays at a third energy level;
generating a first normalize image based on the first flood field image and the third flood field image;
generating a second normalize image based on the second flood field image and the third flood field image;
receiving a first x-ray image generated by x-rays at the first energy level;
receiving a second x-ray image generated by x-rays at the second energy level;
applying the first normalize image to the first x-ray image to generate a normalized first x-ray image;
applying the second normalize image to the second x-ray image to generate a normalized second x-ray image; and
combining the normalized first x-ray image with the normalized second x-ray image to generate a dual energy x-ray image.

17. The method of claim 16, wherein the x-rays at the first energy level have a lower energy level than the x-rays at the second energy level.

18. The method of claim 17, wherein:
generating the first normalize image based on the first flood field image and the third flood field image further comprises:
dividing the first flood field image by the third flood field image to generate a first intermediate image;
calculating a mean of the first intermediate image; and
dividing the first intermediate image by the mean of the first intermediate image to generate the first normalize image; and
generating the second normalize image based on the second flood field image and the third flood field image further comprises:
dividing the second flood field image by the third flood field image to generate a second intermediate image;
calculating the mean of the second intermediate image; and
dividing the second intermediate image by the mean of the second intermediate image to generate the second normalize image.

19. The method of claim 18, further comprising applying a weight factor to the first x-ray image, the weight factor comprising a number between zero and one.

20. The method of claim 19, wherein combining the normalized first x-ray image with the normalized second x-ray image to generate the dual energy x-ray image is calculated according to $I_{DE}=\exp[\ln(I_H*I_{N2})-W*\ln(I_L*I_{N1})]$, where is $I_{DE}$ is the dual energy x-ray image, exp is an exponential function, ln is a natural logarithm function, $I_H$ is the second x-ray image, $I_{N2}$ is the second normalize image, W is the weight factor, $I_L$ is the first x-ray image, and $I_{N1}$ is the first normalize image.

* * * * *